US009320817B2

(12) United States Patent
Walker et al.

(10) Patent No.: US 9,320,817 B2
(45) Date of Patent: Apr. 26, 2016

(54) IRRADIATION APPARATUS FOR INACTIVATING PATHOGENS AND/OR LEUKOCYTES IN A BIOLOGICAL FLUID AND PROCESS

(71) Applicant: MACO PHARMA S.A., Mouvaux (FR)

(72) Inventors: Wolfram Hubert Walker, Rödermark (DE); Frank Tolksdorf, ober-Ramstadt (DE); Thierry Verpoort, Halluin (FR); Francis Goudaliez, Faches Thumesnil (FR); Maurice Behague, Linselles (FR); Arnaud Chavatte, Isbergues (FR)

(73) Assignee: MACO PHARMA S.A., Mouvaux (FR)

( * ) Notice: Subject to any disclaimer, the term of this patent is extended or adjusted under 35 U.S.C. 154(b) by 0 days.

(21) Appl. No.: 14/329,216

(22) Filed: Jul. 11, 2014

(65) Prior Publication Data

US 2015/0030500 A1    Jan. 29, 2015

Related U.S. Application Data

(63) Continuation of application No. 12/665,691, filed as application No. PCT/EP2008/004866 on Jun. 17, 2008, now Pat. No. 8,778,263.

(30) Foreign Application Priority Data

Jun. 22, 2007    (EP) .................................... 07012298

(51) Int. Cl.
*A61L 2/00*    (2006.01)
*A61M 1/14*    (2006.01)
(Continued)

(52) U.S. Cl.
CPC ........... *A61L 2/0047* (2013.01); *A61K 41/0019* (2013.01); *A61L 2/0011* (2013.01); *A61L 2/10* (2013.01); *A61M 1/0277* (2014.02)

(58) Field of Classification Search
CPC ....................................................... A61L 2/00
USPC ......... 422/22, 44; 250/455.11, 454.11, 492.1; 435/238
See application file for complete search history.

(56) References Cited

U.S. PATENT DOCUMENTS

| | | | |
|---|---|---|---|
| 4,469,227 A | 9/1984 | Faust | |
| 4,586,928 A | 5/1986 | Barnes et al. | |

(Continued)

FOREIGN PATENT DOCUMENTS

| | | |
|---|---|---|
| CA | 2632558 | 7/2007 |
| CA | 2634296 | 7/2007 |

(Continued)

OTHER PUBLICATIONS

Prodouz et al., "Use of Laser-UV for Inactivation of Virus in Blood Products," Blood, vol. 70, No. 2, (Aug. 1987); pp. 589-592; National Institutes of Health, Bethesda, MD.

(Continued)

*Primary Examiner* — Monzer R Chorbaji
(74) *Attorney, Agent, or Firm* — Locke Lord LLP; Alan B. Clement; Peter J. Fallon

(57) ABSTRACT

The invention relates to an irradiation apparatus for inactivating pathogens and/or leukocytes in a biological fluid such as a platelet suspension and/or plasma comprising: a casing (2), a support member (3) for carrying at least one irradiation bag (19) containing the biological fluid, a light source (4) comprising two banks of light (5, 6) disposed above and below the support member (3), and an agitating system (25) for moving the support member (3), the light source generating UVC light of suitable intensity to inactivate pathogens and/or leukocytes and the agitation system moving the support member in an orbital path with predetermined amplitude and rotational frequency suitable to expose the whole biological fluid to UVC.

38 Claims, 5 Drawing Sheets

(51) Int. Cl.
*G01N 23/00* (2006.01)
*G01N 21/00* (2006.01)
*A61N 5/00* (2006.01)
*A61K 41/00* (2006.01)
*A61L 2/10* (2006.01)
*A61M 1/02* (2006.01)

(56) References Cited

U.S. PATENT DOCUMENTS

| | | | |
|---|---|---|---|
| 4,952,812 A * | 8/1990 | Miripol | A61L 2/0011 250/455.11 |
| 4,952,818 A | 8/1990 | Erdelyi et al. | |
| 5,030,200 A | 7/1991 | Judy et al. | |
| 5,133,932 A | 7/1992 | Gunn et al. | |
| 5,593,228 A | 1/1997 | Tannenbaum | |
| 5,625,079 A | 4/1997 | Wollowitz et al. | |
| 6,268,120 B1 | 7/2001 | Platz et al. | |
| 6,686,480 B2 | 2/2004 | Wollowitz et al. | |
| 6,809,326 B2 | 10/2004 | Disabito et al. | |
| 8,778,263 B2 * | 7/2014 | Walker | A61K 41/0019 250/454.11 |
| 2001/0046450 A1 | 11/2001 | Laub et al. | |
| 2002/0138066 A1 | 9/2002 | Manica et al. | |
| 2003/0064001 A1 | 4/2003 | Fries et al. | |
| 2003/0072676 A1 | 4/2003 | Fletcher-Haynes et al. | |
| 2003/0228564 A1 | 12/2003 | Edrich et al. | |
| 2004/0186410 A1 | 9/2004 | Davidner et al. | |
| 2005/0202395 A1 | 9/2005 | Edrich et al. | |
| 2007/0085996 A1 | 4/2007 | Mangan et al. | |
| 2007/0164233 A1 | 7/2007 | Mohr | |
| 2009/0155121 A1 | 6/2009 | Mohr et al. | |
| 2010/0133203 A1 | 6/2010 | Walker et al. | |
| 2010/0178200 A1 | 7/2010 | Walker et al. | |

FOREIGN PATENT DOCUMENTS

| | | |
|---|---|---|
| DE | 29801590 | 4/1998 |
| DE | 102005062410 | 8/2007 |
| EP | 0542221 | 5/1993 |
| EP | 0727938 | 8/1996 |
| EP | 0933090 | 8/1999 |
| EP | 1002512 | 5/2000 |
| EP | 1308172 | 5/2003 |
| FR | 2887335 | 12/2006 |
| JP | 2009-534171 A | 9/2009 |
| WO | WO 89/09067 | 10/1989 |
| WO | WO 95/12973 | 5/1995 |
| WO | WO 01/54738 | 8/2001 |
| WO | WO 01/54739 | 8/2001 |
| WO | WO 01/96340 | 12/2001 |
| WO | WO 02/26270 | 4/2002 |
| WO | WO 02/092806 | 11/2002 |
| WO | WO 03/063915 | 8/2003 |
| WO | WO 03/086479 | 10/2003 |
| WO | WO 03/090795 A1 | 11/2003 |
| WO | WO 2004/032782 | 4/2004 |
| WO | WO 2004/033081 | 4/2004 |
| WO | WO 2005/089816 A1 | 9/2005 |
| WO | WO 2006/136698 | 12/2006 |
| WO | WO 2007/076832 | 7/2007 |
| WO | WO 2007/121958 | 11/2007 |
| WO | WO 2008/034476 | 3/2008 |
| WO | WO 2009/000445 A1 | 12/2008 |

OTHER PUBLICATIONS

Andreu et al., "Ultraviolet Irradiation of Platelet Concentrates: Feasibility in Transfusion Practice," Transfusion, vol. 30, No. 5 (1990), pp. 401-406.
Pamphilon, Derwood H., "The Rationale and Use of Platelet Concentrates Irradiated with Ultraviolet-B Light," Transfusion Medicine Reviews, vol. 13, No. 4 (Oct. 1999), pp. 323-333.
Platelets Study Group, "Leukocyte Reduction and Ultraviolet B Irradiation of Platelets to Prevent Alloimmunization and Refractoriness to Platelet Transfusions," The New England Journal of Medicine, (Dec. 25, 1997), vol. 337, No. 26, pp. 1861-1869.
Kallenbach, "Inactivation of Viruses by Ultraviolet Light," Morgenthaler J-J(ed), Virus Inactivation in Plasma Products, Curr. Stud. Hematol Blood Transfus. Basel, Karger 1989, No. 56, pp. 70-82.
Hart et al., "Inactivation of Viruses during Ultraviolet Light Treatment of Human Intravenous Immunoglobulin and Albumin," Vox Sang, (1993), 64:82-88.
Chin, "Virucidal Short Wavelength Ultraviolet Light Treatment of Plasma and Factor VIII Concentrate: Protection of Proteins by Antioxidants," Blood, vol. 86, No. 11 (Dec. 1, 1995), pp. 4331-4336.
Handbook of Transfusion Medicine, 4th Edition, Published 2007, Edited by DBL McClelland, Scottish National Blood Transfusion Service, Edinburgh, Published by United Kingdom Blood Services, ISBN 0113226772.
International Search Report issued on Feb. 12, 2008, for corresponding International Application No. PCT/EP2008/004866.
Written Opinion of the International Searching Authority received Jan. 7, 2010 for corresponding International Application No. PCT/EP2008/004866.
Canadian Office Action and Examination Search Report dated Apr. 24, 2015.

* cited by examiner

IRRADIATION APPARATUS FOR INACTIVATING PATHOGENS AND/OR LEUKOCYTES IN A BIOLOGICAL FLUID AND PROCESS

This application is a continuation of application Ser. No. 12/665,691, filed Dec. 18, 2009, now U.S. Pat. No. 8,778,263, which is a 371 of PCT/EP08/04866, filed Jun. 17, 2008, which claims priority to EPO application no. 07012298.1 filed Jun. 22, 2007.

The invention relates to an irradiation apparatus for inactivating pathogens and/or leukocytes in a biological fluid such as a platelet suspension and/or human plasma, and a process for inactivating pathogens and/or leukocytes using such an apparatus.

In the field of transfusion, blood is collected from donors and separated into its different components including red blood cells, plasma and platelet concentrates. These components are subjected to different treatment, including leukocyte removal and pathogen and/or leukocyte inactivation to improve their quality and safety.

German patent application 10 2005 062 410.3 filed 23 Dec. 2005 by the present applicant as co-applicant teaches a process for the reduction of pathogens and/or leukocytes in platelet concentrates using flexible UV-transparent blood bags, the contents of which and particularly the process described therein is made of full reference for the present application. The flexible blood bags are irradiated while agitating the bag.

It is known from EP 1 308 172 A1 that UV in the range from 260 to 300 nm can inactivate viruses in blood derived products such as plasma or serum, without damaging proteins. It is also indicated that UVC destroys valuable proteins. No irradiation apparatus is described in this document.

US 2001/0046450 A1 discloses an apparatus for inactivating contaminants in blood products. The blood product is guided past a source of UV-C radiation whereby the flow of the blood product is controlled to receive irradiation doses of 230-400 J/m$^2$. The apparatus includes an emitter of type C ultraviolet radiation placed so as to emit type C radiation toward the blood product in a quartz tube or a tube made of polymer material which does not absorb type C radiation. The apparatus also includes a pump for moving the blood in the tube and means for maintaining homogeneous flow in the tube. This apparatus is not suitable for irradiating blood placed in a bag.

U.S. Pat. No. 6,696,023 discloses an apparatus for irradiating a suspension of platelets contained in a blood bag with UVB light to reduce their immunogenicity. The apparatus comprises a tray to support the blood bag and a pair of UV lights arranged above and below the tray to irradiate the bag from both sides. This apparatus does not contain any agitation means.

A similar apparatus is described in US 2003/0072676 and WO 03/090795 in relation with an inactivation process comprising the steps of contacting the blood with a photosensitizer (riboflavine) and irradiating the resulting mixture with visible or UV light. The apparatus comprises a tray for supporting the blood bag, which is moveable in order to oscillate thereby agitating and/or mixing the content of the blood bag.

The invention provides an apparatus for inactivating pathogens and/or leukocytes in a biological fluid such as a platelet suspension and/or plasma as described in the claims or herein under, in which the biological fluid contained in a blood bag is homogenously and uniformly irradiated with a light of suitable wavelength and intensity to inactivate pathogens and/or leukocytes, without adding any pathogen inactivating substances.

A first aspect of the present invention is an irradiation apparatus for inactivating pathogens and/or leukocytes in a biological fluid such as a platelet suspension comprising:
a casing,
a support member for carrying at least one irradiation bag containing the biological fluid,
a light source comprising two banks of light disposed above and below the support member, and
an agitating system for moving the support member,
wherein the light source generates UVC light of suitable intensity to inactivate pathogens and/or leukocytes and the agitation system moves the support member in an orbital path with predetermined amplitude and rotational frequency suitable to expose the whole biological fluid to UVC.

According to a preferred aspect of the invention the movable tray builds the support member, wherein the tray may comprises a frame and a bottom, at least a part of which is permeable to UVC to allow irradiation of the biological fluid placed upon the bottom. According to one embodiment the bottom of the tray is at least in part made of quartz. The frame may furthermore comprise a holder for holding a bag. The holder can have a V-shape form and/or may be in the form of a chamber with a cover.

According to a preferred embodiment the agitation system comprises a motor with a shaft perpendicular to the plane of the support member, the shaft having an eccentric pin coupled to the support member through a bearing.

The agitation system preferably comprises a guiding device for constraining the motion of the support member in an orbital path of predetermined amplitude. According to one embodiment the guiding device comprises a guiding frame and guiding members cooperating with lateral and longitudinal slides.

The support is preferably agitated with a frequency of from 50 to 150 rpm, in particular from 70 to 130 rpm and most preferred 108 rpm, by way of example in a circular path having a diameter of from 0.2 to 8 cm.

The light source used emits light in the wavelength of from 200 to 350 nm, preferably 200 to 270 nm and most preferred about 254 nm and independent thereof may provide by way of example a total energy of from 0.01 to 2 J/cm$^2$. The intensity of the radiation can vary from 1 to 20 mW/cm$^2$.

The invention is furthermore directed to an assembly for inactivating pathogens and/or leukocytes in a biological fluid such as a platelet suspension comprising the irradiation apparatus described above and at least one irradiation bag containing a biological fluid on the support member. The irradiation bag is made from flexible plastic material substantially transparent to UVC and preferably has a volume capacity of at least 10 times of the volume of the biological fluid contained in the irradiation bag. The irradiation bag generally does not contain a photoinactivating substance. When a platelet suspension is irradiated the platelet suspension may furthermore comprises plasma.

Another aspect of the invention is a process for inactivating pathogens and/or leukocytes in a biological fluid such as a platelet suspension and/or plasma, comprising:
providing an irradiation apparatus according to the first aspect of the invention,
placing at least an irradiation bag containing a biological fluid on the support member,
irradiating the irradiation bag with UVC under orbital agitation preferably with a rotational frequency between 50 and 150 rpm by way of an orbital path (e.g. diameter of from 0.2 to 8 cm) or a circular path with a diameter of from 2 to 5 cm.

Figure 3:
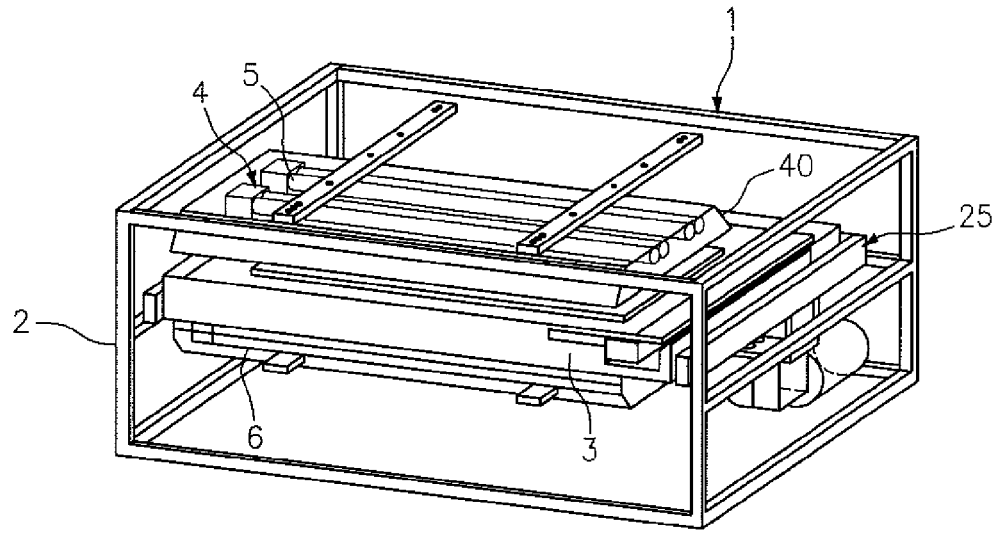
FIGS. 3 and 4 show the inside of the apparatus of FIG. 2, with the slidable tray in and out of the casing, respectively.

According to a first aspect of the invention, FIG. 3 shows an apparatus 1 for inactivating pathogens and/or leukocytes in a biological fluid such as a platelet suspension and/or plasma comprising a casing 2, a support member 3 for carrying at least one irradiation bag containing the biological fluid, a light source 4 generating an UVC light of suitable intensity to inactivate pathogens and/or leukocytes, and an agitation system 25 for moving the support member 3 in an orbital path with predetermined amplitude and rotational frequency.

The light source 4 comprises two banks of light 5,6 disposed above and below the support member 3.

Figure 1:
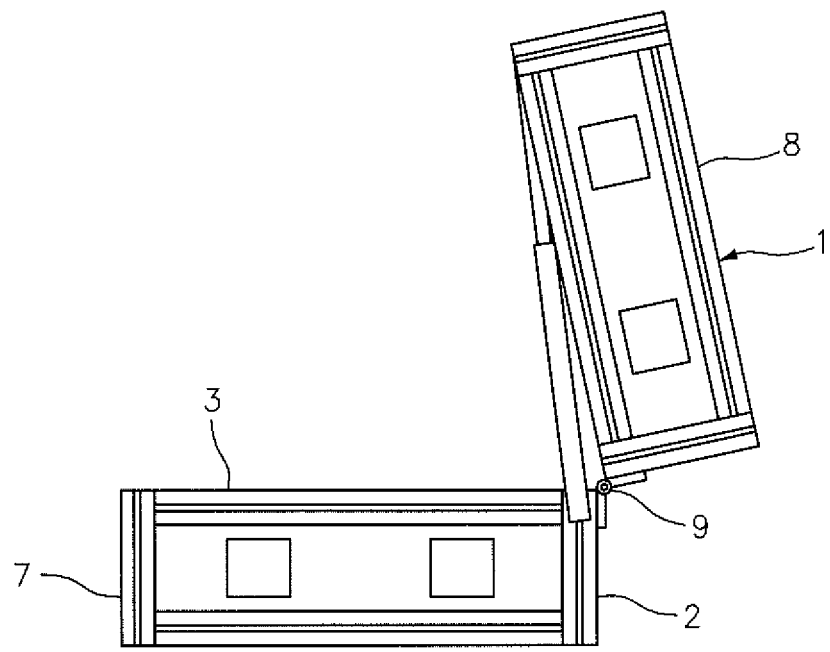
FIG. 1 represents a lateral view of an irradiation apparatus with a housing and a cover according to one embodiment of the invention.

The casing 2 comprises an upper and a lower part. In a particular embodiment represented in FIG. 1, the lower part is in the form of a housing 7 comprising a light source and the support member 3. The upper part is in a form of a cover 8 comprising the second light source. The cover 8 is connected via a hinge 9 to the housing 7 to allow the opening and closing of the casing 2.

Figure 2:
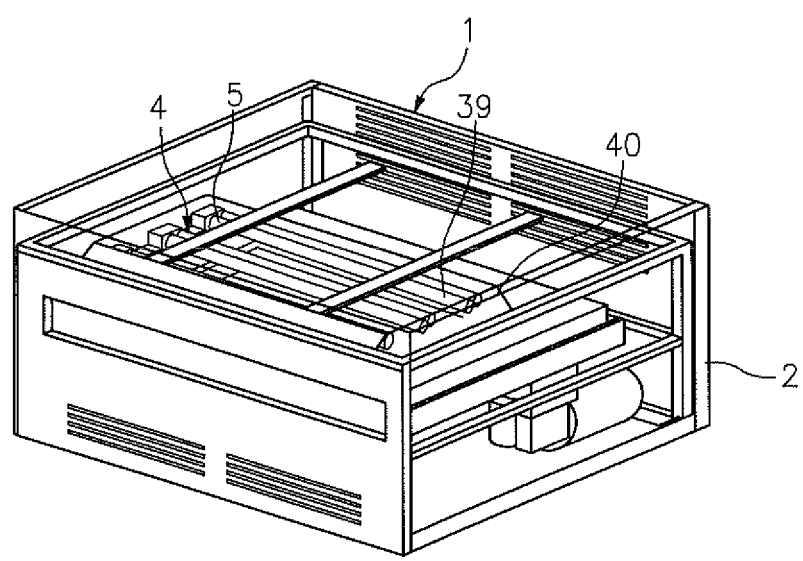
FIG. 2 represents a perspective view of an irradiation apparatus with a slidable tray according to another embodiment of the invention.

In another embodiment represented in FIG. 2, the casing 2 consists of one piece and comprises a movable support member 3 for the blood bag. The support member in that case can move in and out of the casing 2 as explained below.

Since exposure to UVC can be harmful for men, animals and plants, the casing 2 is light impermeable. In particular, the apparatus 1 comprises a safety locking mechanism so that the illumination starts only when the cover 8 is locked on the housing (FIG. 1) or when the movable support member 3 is in the casing 2 (FIG. 2).

The light source 4 comprises two banks of light 5,6 disposed above and below the support member 3 to provide an irradiation on both sides of the bag containing the platelet suspension.

Figure 4:
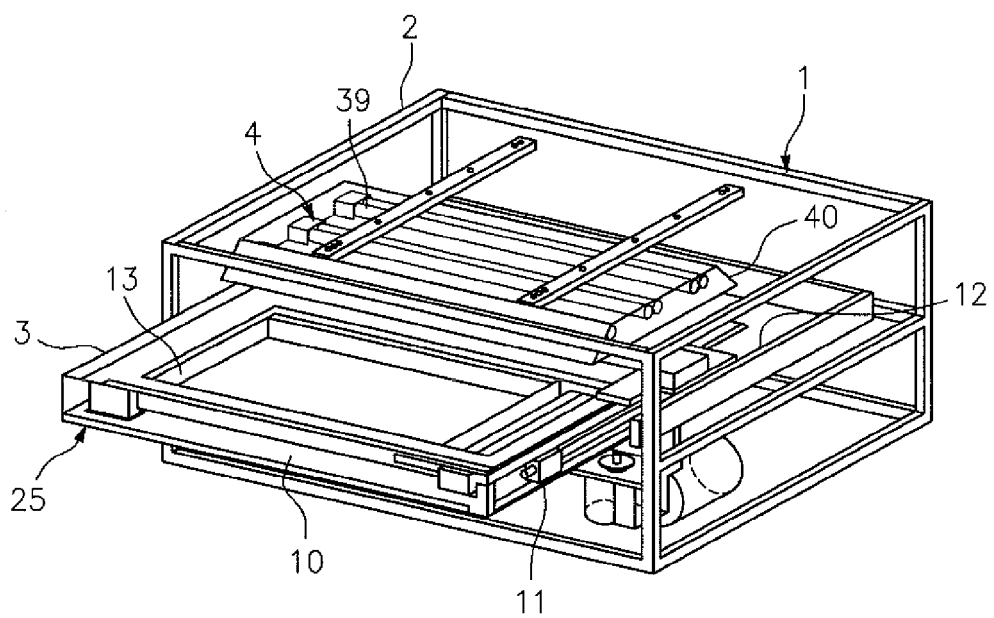

In particular, the support member is in a form of a tray 10 which is moved manually or automatically in and out of the casing 2 by horizontal rotation, translation or combination thereof. In particular, as shown in FIGS. 3 and 4, the tray 10 comprises slides 11 on lateral sides which cooperate with rails 12 arranged into the casing 2. As shown in FIG. 4, when the tray is out of the casing, a blood bag can easily be placed on or removed from the tray. When the tray 10 is in the casing 2, it is arranged between the two banks of light 5,6 to allow the blood bag to be irradiated from both sides.

Advantageously, a safety mechanism allows the irradiation to start only when the tray 10 is in the casing 2.

Figure 6:
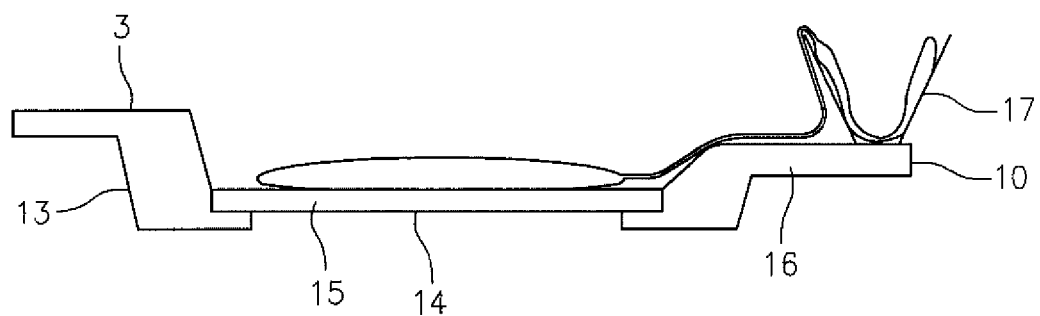
FIG. 6 represents a side view of a support member comprising a holder.

As shown in FIG. 6, the tray comprises a frame 13, for example made of metal, and a bottom 14, at least a part of which is permeable to UVC to allow the irradiation of the platelet suspension.

Figure 5:
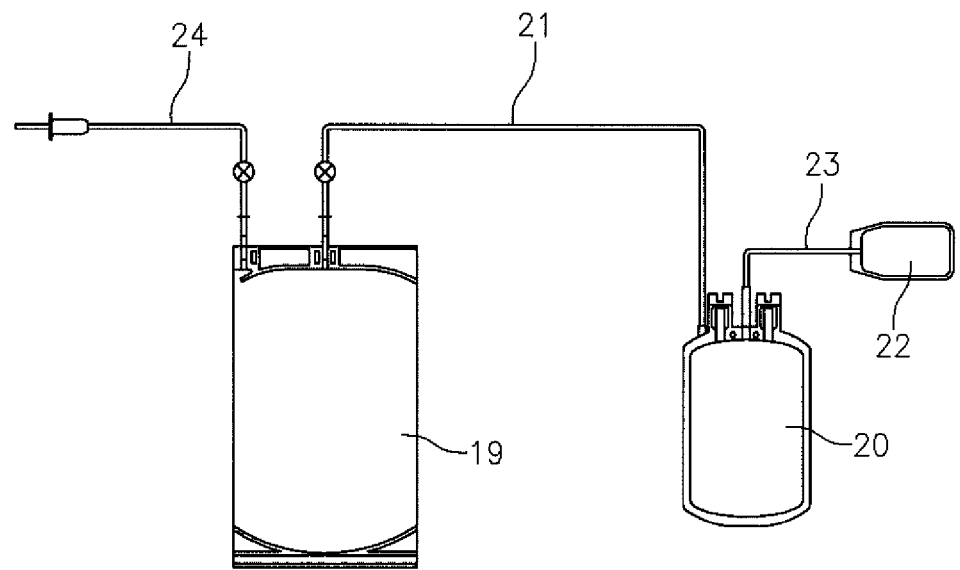
FIG. 5 represents a blood bag system comprising an irradiation bag containing a platelet suspension to be irradiated.

The tray 10 is suitable to dispose a blood bag system as represented in FIG. 5. The blood bag system comprises an irradiation bag 19 and at least another blood bag, such as a platelet storage bag 20 connected to the irradiation bag via a first tubing 21. The blood bag system can also comprises a sampling bag 22 connected to the storage bag via a second tubing 23. The sampling bag is intended to receive a sample of the irradiated platelet suspension contained into the storage bag 20. The irradiation bag 19 is connected to a third tubing 24, which can be sterilely connected to a bag containing a platelet suspension to be irradiated.

In a particular embodiment, the blood bag system comprises at least an irradiation bag 19 for irradiation with UVC light and optionally a storage bag 20 for storage of the irradiated platelet suspension in which the platelet suspension can be stored for example for up to 10 days without clinically significant reduction of the therapeutic quality.

The irradiation bag 19 is made of an UVC-transparent plastic material. Suitable polymer materials are polyolefins and ethylene vinyl acetate (EVA), extruded or calendered to wall thicknesses of 0.8 mm or less, in particular about 0.5 mm or less. The bag is formed by sealing foils made of UVC-transparent plastic material such that the irradiation bag 19 has a substantially flat inside. In particular, the bag is made of material that has no adsorption maximum in the range of 200 to 270 nm. Thickness and quality of the EVA material after sterilization is such, that it shows minimal adsorption of UVC-light. Particularly preferred are EVA polymers of low polymerization degree and low crosslinking. The UV-light adsorption may also be influenced by the acetylation degree of the EVA.

Particularly, the irradiation bag 19 is not completely filled with biological fluid such as platelet suspension. The irradiation bag is filled at most 30% and preferably at most 20% and most preferred 1 to 10% (each in Vol. %) of its capacity.

The volume capacity of the irradiation bag 19 is defined as maximum filling volume obtained by gravity flow of water into the bag at 1 m height difference.

For example, the volume capacity of the irradiation bag is 5000 ml and the actual storage volume of biological fluid is 500 ml. Therefore, the ratio of volume capacity of the irradiation bag to biological fluid volume is factor 10.

Therefore, the irradiation bag 19 after filling with biological fluid is only a few millimeters thick, such as less than 5 mm. For example, bags of a dimension of 19×38 cm filled with 200 to 300 ml of biological fluids have a thickness of below 5 mm.

Moreover, the irradiation bag 19 comprises one or more inlet tubes and/or outlet tubes and is provided with means for preventing the biological fluid contained in the irradiation bag 19 to be treated to enter into and/or to access the inlet and/or outlet tubes to avoid dead area formed inside the irradiation bag 19 in or around the tubes.

For example, the inlet tubes and/or outlet tubes comprise at least one clamp-off part, plug or break-off part as a closing for the tube end extending into the irradiation bag, preferably located at the inner end of the tube, in particular the outlet tube in which case the closing is openable.

In another example, the irradiation bag 19 (FIG. 5) comprises a partial seal extending from one edge of the bag to an adjacent edge thereof. When the seal is completed, the seal creates a first sealed compartment enclosing the opening of the inlet tube and a second sealed compartment comprising the biological fluid. This first sealed compartment prevents the biological fluid in the second sealed compartment to enter the inlet tube. In that way, the irradiation bag does not contain any dead area, ensuring that all biological fluid is agitated and irradiated during the inactivation process.

Moreover, as shown in FIG. 5, the seal enclosing the inlet tube at one edge of the irradiation bag 19 is symmetrical to at least another edge, thereby providing a symmetrical irradiation bag. This particular shape improves the agitation of the content of the bag.

Advantageously, the irradiation bag 19 also comprises an outlet tube provided with a plug, ensuring that no biological fluid enters the outlet tube. For discharging the biological fluid into the storage bag 20, the plug is simply removed from the outlet tube by pressing manually the outlet tube to expel the plug 18 into the bag (FIG. 5).

The storage bag 20 may be made of PVC material comprising DEHP, citrate esters or trioctyl trimellitate (TOTM) as plasticizer. However, according to a preferred embodiment, the storage bag 20 consists of the same UVC-transparent plastic material as the irradiation bag 19.

When the biological fluid is a platelet suspension, it is important that the storage bag 20 shows gas permeability, in particular oxygen and carbon dioxide permeability, and platelet compatibility, so that the platelet suspension can be stored for up to 10 days, preferably under a slight agitation.

It was also found that, when the biological fluid is a platelet concentrate, optionally at least part of the plasma contained in the platelet concentrate may be substituted by an aqueous salt solution to form a suspended platelet concentrate, which is suitable for platelet storage.

A preferred aqueous salt solution is SSP+ as marketed by MacoPharma. The plasma in the platelet concentrate to be irradiated may be substituted by 50 to 95 weight %, preferably 70 to 80 weight % with SSP+.

However, other suitable platelet storage solutions may also be used, which replace the plasma for storage.

The bag system may be sterilized by standard techniques like steam or ethylene oxide treatment or by β-rays irradiation, so that the bags and tubes allow sterile preparations after pathogen reduction.

In a particular embodiment represented in FIG. 6, the bottom 14 of the tray 10 comprises a plate 15 permeable to UVC, for example made of quartz. The size of the plate 15 is suitable to receive the irradiation bag 19.

Figure 7:
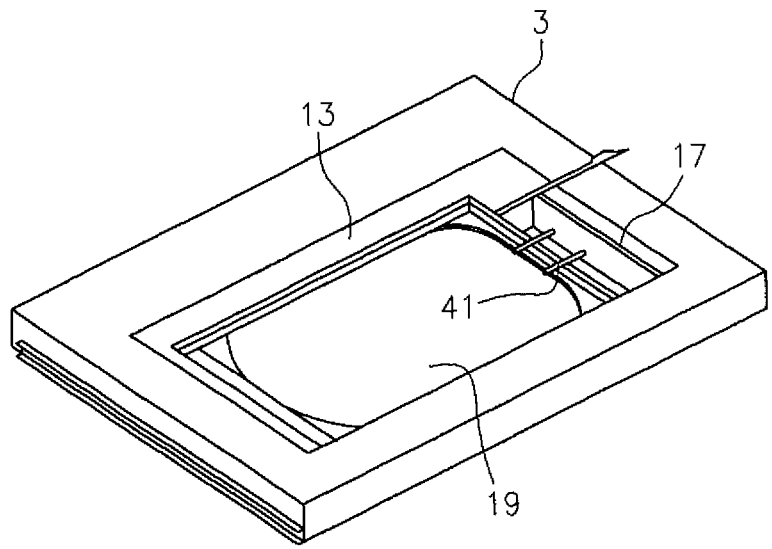
FIG. 7 represents a side view of a support member comprising a chamber with a cover in an open position.

The frame 13 comprises a part 16 which is impermeable to UVC. Part of the blood bag system, including bags 20 and tubings, which does not need to be irradiated, are placed in a holder 17 during the irradiation. The holder is arranged on the impermeable part 16 of the frame 13. The holder is for example a metallic support in a V-shape (FIG. 6) or a chamber which can be closed with a cover (FIG. 7). The bags are preferably rolled into the chamber. The holder is provided with channels 41 to arrange tubings connecting the irradiation bag 19 with the remaining tubings and/or bags of the blood bag system.

The storage bag 20 for preserving the platelet suspension is made of a material which can be altered by the UVC irradiation, thereby compromising the quality of the stored platelets. For example, the storage bag 20 is made of PVC plasticized with trioctyltrimellitate (TOTM) or butyryl trihexyl citrate. Therefore, in a particular realization, the part of the blood bag system in the holder 17 is prevented from being irradiated. For example, when the holder is in the form of a chamber with a cover, the cover hermetically closes the chamber. When the holder 17 is in the form of a V-shaped support, the apparatus comprises a wall (not represented) separating the light source from the holder 17.

When the UVC permeable plate 15 is made of quartz and the irradiation bag 19 is made of a non PVC material such as EVA, there is no need to fix the bag 19 on the plate 15 because the bag adheres to the plate.

In other cases, pinches or clamps can be provided to fixedly maintain the irradiation bag during the irradiation under agitation.

However, the irradiation bag 19 is not maintained between two horizontal plates. Indeed, the bag should be in an uncompressed state, allowing the platelet suspension to move freely therein during agitation.

In a particular embodiment (FIG. 6), the surface of the tray 10 does not contain any sharp angles to avoid kinking or folding of the tubing 21 connecting the irradiation bag 19 and the storage bag 22. The surface of the tray 10 consists of plane or rounded portions with smooth edges.

According to the invention, the irradiation apparatus also comprises an agitation system 25 for moving the support member 3 in an orbital path. The orbital motion allows the biological fluid to be sufficiently and uniformly exposed to UVC during the irradiation step. The agitation compensates the low penetration of UVC in platelet suspension. The agitation is realized in the horizontal plane, that is the plane in which the irradiation bag 19 is lying flat.

The "orbital motion" refers to motion that moves back and force between two points in a continuous manner, wherein the route of the backward movement may either partially overlap or not overlap the route of the forward movement.

The orbital motion has a predetermined amplitude and rotational frequency suitable to expose the whole biological fluid to UVC. This particular motion produces an intermittent fluid layer into the irradiation bag 19 having a thickness sufficiently low to be penetrated by UVC as well as a circulation of platelets inside the irradiation bag such that platelets come onto the surfaces of the fluid layer to receive UVC irradiation.

In an embodiment, the path is elliptic and has a width and a length comprised between 2 and 5 cm. In another embodiment, the path is circular with a diameter of from 0.2 to 8 cm, preferably 2 to 5 cm. For example, the circular path has a width of about 4 cm.

The agitation system provides a strong rotational frequency of from 50 to 150 rpm (revolutions per minute), preferably 70 to 130 rpm, most preferred 108 rpm. The frequency can be adjusted electronically or by a potentiometer connected to the motor.

By agitating the support member 3, the content of the irradiation bag 19 is agitated. The thickness of the platelet suspension varies in waves, allowing the biological fluid to be fully illuminated. Intermittently, the liquid thickness in the irradiation bag is very low, smaller than about 5 mm, allowing penetration into the platelet suspension.

This high agitation rate also homogenizes the content of the irradiation bag such that the biological fluid is homogeneously irradiated.

Moreover, the irradiation intensity of the light source may varies along the light bulb. By having a high agitation amplitude and rotational frequency, the content of the bag is moving inside the bag and along the light source, providing a homogeneous irradiation.

Figure 8:
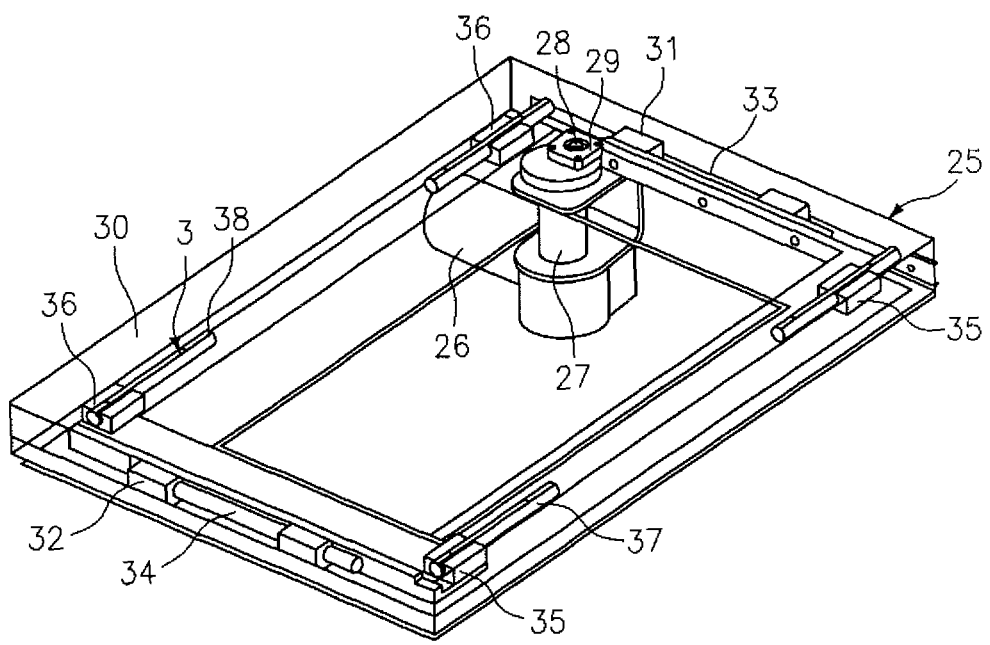
FIGS. 8 and 9 represent views from above and below, respectively, of the support member and the agitation system of the apparatus of FIG. 2.
Figure 9:
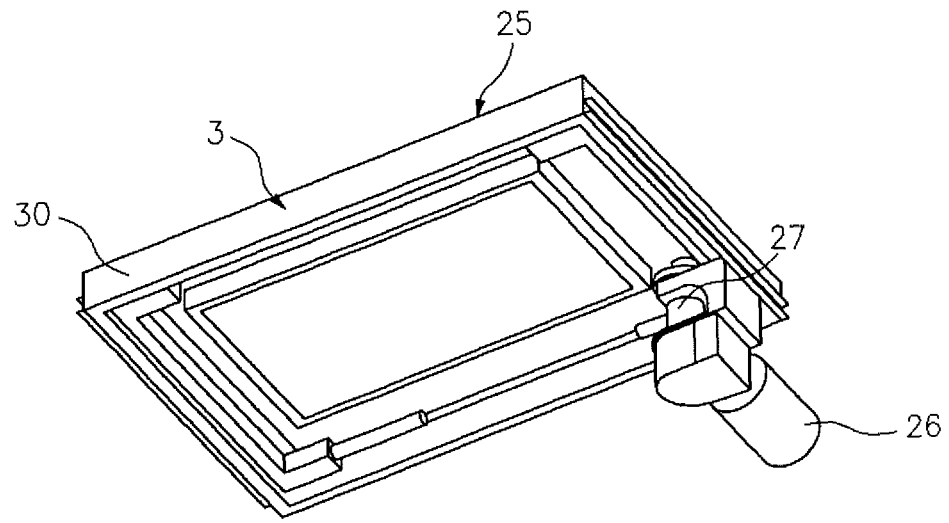
Figure 10:
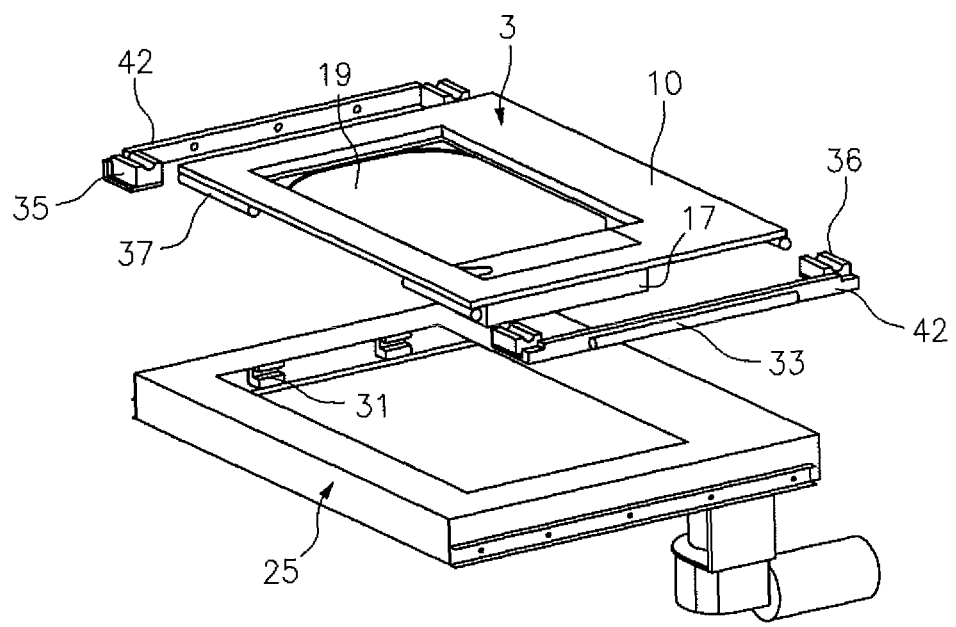
FIG. 10 represents an exploded view of the support member and the agitation system of the apparatus of FIG. 2

As shown in FIGS. 8 to 10, the motion of the support member 3 is produced by a motor 26 having a shaft 27 perpendicular to the plane of the support member 3. The shaft has an eccentric pin 28. Rotation of the shaft 27 produces an orbit of the pin 28. The pin 28 is coupled to the support member through a bearing 29.

The agitation system 25 also comprises a guiding device for constraining the motion of the support member 3 in an orbital path of a predetermined amplitude. The guiding device comprises a guiding frame 30, larger than the frame of the tray 10, on which the motor 26 is fixedly attached.

A first and second lateral guiding member 31,32 is mounted on the lateral sides of the guiding frame 30. In a particular embodiment, each guiding member 31,32 includes two separated rails. These guiding members are intended to receive a first and second lateral slide 33,34, respectively. Lateral slides 33,34 are slidable into the guiding members.

These lateral slides 33,34 stand together a first and second longitudinal guiding member 35,36 via a plate 42. In particular, each guiding member 35,36 includes two separated rails. These guiding members are intended to receive a first and second longitudinal slide 37,38, respectively, fixed on the support member 3. Longitudinal slides 37,38 are slidable into the longitudinal guiding members 35,36.

In the embodiment represented in FIG. 8, the agitation system 25 is movable in and out of the casing 2 with the support member 3.

In another embodiment not represented, the agitation system 25 is fixedly mounted into the casing 2. When the tray 10 is slid into the casing 2, it engages on the eccentric motor.

No element of the agitation system 25 obstructs the light path between the light source and the irradiation bag. In particular, it is noted that the motor assembly is arranged next to the permeable plate 15 receiving the irradiation bag 19.

Other systems can be used to produce orbital motion. In particular, the orbital motion can be produced by two or more different shafts with eccentric pins, connected to each other with a belt. In another embodiment, two or more motors can be used. For example, the lateral and longitudinal shafts are controlled by two linear motors to produce the orbital motion.

The irradiation apparatus 1 comprises a light source 4 generating UVC light. The light source comprises an upper bank 5 of light in the upper part of the casing 2 and a lower bank 6 of light in the lower part of the casing 2.

The support member 3 carrying the blood product such as a platelet suspension is disposed between the upper and lower bank 5,6 in order to provide both sided irradiation.

In particular, each light bank comprises three U-shaped bulbs 39 emitting UVC in the range of 200 to 350 nm, preferably 200 to 270 nm, in particular about 254 nm. Independent thereof the UVC source delivers from 1 to 30 mW/cm$^2$, particularly 6-9 mW/cm$^2$. The total energy delivered to the irradiation bag is up to 10 J/cm$^2$. An example of a suitable bulb includes Philips TUV PL-L 55W/HF.

Thanks to the U-shape of the bulbs 39, the plugs are placed only on one side of the casing 2, which facilitate the electric connections.

Reflectors 40 in polished aluminium are provided behind the bulbs and allow the light to diffuse in the direction of the irradiation bag 19 more homogeneously. For facilitating the maintenance of the bulbs, light banks 5,6 can be mounted on a slide, as shown in FIGS. 3 and 4.

The light dose for irradiation may be up to 10, preferably between 0.01 and 2 J/cm$^2$, however, depending on the frequency range and filters used and the PC layer thickness in the irradiation bag, other energies may be used. This also depends on whether the light has been generated by a quartz lamp, light emitting diodes (LEDs) or flash lights, e.g. by Eximer lamps.

The rotational frequency of the agitation is an important parameter in the irradiation process for inactivating pathogens and/or leukocytes of the platelet suspension.

If agitation does not occur as predetermined, the platelet suspension may be insufficiently or non-uniformly irradiated, resulting in an insufficient inactivation of the pathogens.

The apparatus 1 comprises a speed control system to ensure that the agitation is occurring and/or has occurred as predetermined.

The speed control system checks the rotational frequency of the tray and controls that the tray has been agitated as predetermined.

For example, the speed control system checks the speed of rotation of the motor 26 and/or the frequency of rotation of the support member 3.

In a particular realization, a signal emitting member and a signal sensing member are arranged one in a fixed position into the casing or agitation system and the other on the movable tray. When the tray is agitated, the sensing member receives periodically the signal emitted by the emitting member. The speed control system sends signals to a microprocessor. Based upon the number of signals received per time unit, the frequency of rotation can thus be easily determined.

In a second realization, the speed control system comprises a signal emitting/sensing member, such as an inductive or optical sensor, arranged to detect the passage of the support member 3 in front of it.

Energy of the irradiation is also a parameter of great importance in the inactivation process. To control the light energy delivered to the platelet suspension, light sensors are provided in the apparatus. These sensors also detect the presence of a defective bulb 39.

In particular, light sensors are arranged at each extremity of the U-shaped bulbs to control the total energy of light delivered to the irradiation bag. For example, one light sensor is placed between two bulbs 39, such that two sensors control the three bulbs of one bank 5,6.

When the apparatus is in use, the intensity of light detected by the light sensors is not linear but varies in a wave pattern. These variations depend, among others, on the reflection of light inside the apparatus, on the agitation and/or on the transmission of light through the irradiation bag 19. By sensing these intensity variations, the absence of the irradiation bag 19 on the support member 3 as well as the parameters of the agitation could be checked. The checking adds to the control performed by the speed control system.

In a particular embodiment, the temperature inside the irradiation apparatus is controlled by sensors and fans. The temperature should not rise above 25° C. to prevent damage to platelets.

The irradiation apparatus comprises a user interface to assist the user in the use of the apparatus. The user interface comprises a screen and buttons.

The irradiation apparatus comprises a traceability system: a microprocessor provides information such as the irradiation status (treated platelet or invalid treatment in a case of irradiation and/or agitation interruption), the date and time of irradiation, apparatus serial number, energy/intensity curve, temperature curve, etc. These information can be implemented into code bar and/or RFID labels.

In a particular embodiment, a RFID tag can be placed in the blood bag system, e.g. the storage bag 20 can be labelled with a RFID tag. The irradiation apparatus 1 comprises a RFID writer/reader to ensure the traceability of the blood component and irradiation process.

According to a second aspect of the invention, a process for inactivating pathogens and/or leukocytes in a platelet suspension with the help of the irradiation apparatus of the invention is now described.

Pathogens include bacteria, viruses, parasites, spores, fungi or porotozoa.

The inactivation process comprises the steps of
providing the irradiation apparatus according to the invention,
placing at least an irradiation bag 19 containing a suspension of platelet on the support member 3,
irradiating the irradiation bag with UVC under orbital agitation.

In a particular embodiment, the irradiation bag is filled with at most 30% of the volume capacity of the bag, preferably with at most 10%. For example, a bag having a volume capacity of 5 l is filled with about 500 ml.

The biological fluid is a platelet suspension such as a platelet concentrate or a pool of 3 to 8 platelet concentrates. The platelet suspension comprises plasma, which may be substituted with a platelet storage solution in an amount of at least 25%. In particular, 70% of the plasma is replaced by a platelet storage solution. For example, the platelet storage solution is the solution SSP+ commercialized by MacoPharma. The SSP+ solution comprises (in g/l):

Na-Citrate $2H_2O$: 3.18; Na-Acetate $3H_2O$: 4.42; Na-Phosphate $2H_2O$: 1.05; Di-Na-Phosphate: 3.05; KCl: 0.37; $MgCl2$ $6H_2O$: 0.3; NaCl: 4.05 and Water to 1000 ml.

In another embodiment, the biological fluid is plasma or human plasma proteins.

According to the invention, the irradiation bag preferably does not contain any inactivating, photosensitive, photochemical or photodynamically active compound.

In the process of inactivation the light source emits light in the wavelength of from 200 to 350 nm, preferably 200 to 270 nm and most preferred about 254 nm. The UVC directly activates nucleotides of pathogens such as viruses and bacteria and therefore destroys the function and replication of such pathogens.

The light source provides a total energy of up to 10, preferably from 0.01 to 2 $J/cm^2$.

The irradiation bag on the support member is moved at a rotational frequency comprised between 50 and 150 rpm, preferably 100 rpm.

The orbital path is in a shape of a circle with a diameter comprised between 0.2 and 8 cm, particularly between 2 and 5 cm.

These predetermined rotational frequency and amplitude of the orbital path provides varying layer thicknesses into the irradiation bag, thereby allowing UVC to penetrate into the platelet suspension.

The invention claimed is:

1. An irradiation apparatus for inactivating pathogens and/or leukocytes in a biological fluid such as a platelet suspension comprising:
   a casing,
   a support member for carrying at least one irradiation bag containing the biological fluid, the irradiation lying flat and horizontally and in an uncompressed state,
   a light source comprising two banks of light disposed above and below the support member, and
   an agitating system for moving the support member, wherein the light source generates UVC light to inactivate pathogens and/or leukocytes and the agitation system moves the support member in an orbital path with predetermined amplitude and rotational frequency suitable to expose the whole biological fluid to UVC, wherein said agitation system is operable to move the support member at a frequency of 70 rpm and above, and the agitation system comprises a motor having a shaft perpendicular to the plane of the support member, the shaft having an eccentric pin coupled to the support member through a bearing.

2. The apparatus of claim 1, wherein the support member is in the form of a movable tray.

3. The apparatus of claim 2, wherein the tray comprises a frame and a bottom, at least a part of which is permeable to UVC to allow the irradiation of the biological fluid.

4. The apparatus of claim 3, wherein the bottom of the tray comprises a plate made of quartz.

5. The apparatus of claim 3, wherein the frame comprises a holder for holding at least one bag.

6. The apparatus of claim 5, wherein the holder is a V-shape support.

7. The apparatus of claim 5, wherein the holder is a chamber with a cover.

8. The apparatus of claim 1, wherein the agitation system further comprises a guiding device for constraining the motion of the support member in an orbital path of predetermined amplitude.

9. The apparatus of claim 8, wherein the guiding device comprises a guiding frame and guiding members cooperating with lateral and longitudinal slides.

10. The apparatus of claim 1, wherein the agitation system moves the support member at a frequency of from about 108 rpm and above.

11. The apparatus of claim 1, wherein the agitation system moves the support member in a circular path having a diameter of from 0.2 to 8 cm.

12. The apparatus of claim 1, wherein each light bank comprises U-shaped bulbs emitting UVC in the range of 200 to 270 nm.

13. The apparatus of claim 1, wherein the light source delivers an intensity of from 1 to 20 $mW/cm^2$.

14. The apparatus of claim 1, further comprising a speed control system to check the rotational frequency of the support member.

15. The apparatus of claim 14, wherein the speed control system checks the rotational speed of the motor.

16. An assembly for inactivating pathogens and/or leukocytes in a biological fluid comprising an irradiation apparatus according to claim 1, and at least one irradiation bag containing a biological fluid on the support member.

17. The assembly according to claim 16, wherein the irradiation bag is made of a flexible plastic material substantially transparent to UVC.

18. The assembly according to claim 16, wherein the irradiation bag has a volume capacity of at least 10 times of the volume of the biological fluid contained in the irradiation bag.

19. The assembly of claim 16, wherein the biological fluid is a platelet suspension.

20. The assembly according to claim 16, wherein the thickness of the biological fluid in the irradiation bag during agitation is intermittently smaller than about 5 mm.

21. The apparatus of claim 1, wherein each light bank comprises U-shaped bulbs emitting UVC of about 254 nm.

22. An irradiation apparatus for inactivating pathogens and/or leukocytes in a biological fluid such as a platelet suspension comprising:
   a casing,
   a support member for carrying at least one irradiation bag containing the biological fluid, the irradiation lying flat and horizontally and in an uncompressed state, a light source comprising two banks of light disposed above and below the support member, and an agitating system for moving the support member, wherein the light source generates UVC light to inactivate pathogens and/or leukocytes and the agitation system moves the support member in an orbital path with predetermined amplitude and rotational frequency suitable to expose the whole biological fluid to UVC, wherein said agitation system is operable to move the support member at a frequency of 70 rpm and above, and further comprising a speed control system to check the rotational frequency of the support member, wherein the speed control system comprises a signal emitting member and a signal sensing member arranged in a fixed position into the casing and/or agitation system and on the tray.

23. An irradiation apparatus for inactivating pathogens and/or leukocytes in a biological fluid such as a platelet suspension comprising:

a casing, a support member for carrying at least one irradiation bag containing the biological fluid, the irradiation lying flat and horizontally and in an uncompressed state, a light source comprising two banks of light disposed above and below the support member, and an agitating system for moving the support member, wherein the light source generates UVC light to inactivate pathogens and/or leukocytes and the agitation system moves the support member in an orbital path with predetermined amplitude and rotational frequency suitable to expose the whole biological fluid to UVC, wherein said agitation system is operable to move the support member at a frequency of 70 rpm and above, and further comprising at least one light sensor to control at least the light energy delivered by the light source.

24. An irradiation apparatus for inactivating pathogens and/or leukocytes in a biological fluid such as a platelet suspension comprising:

a casing, a support member for carrying at least one irradiation bag containing the biological fluid, the irradiation lying flat and horizontally and in an uncompressed state, a light source comprising two banks of light disposed above and below the support member, and an agitating system for moving the support member, wherein the light source generates UVC light to inactivate pathogens and/or leukocytes and the agitation system moves the support member in an orbital path with predetermined amplitude and rotational frequency suitable to expose the whole biological fluid to UVC, wherein said agitation system is operable to move the support member at a frequency of 70 rpm and above, and further comprising a RFID reader/writer.

25. A process for inactivating pathogens and/or leukocytes in a biological fluid, comprising: providing an irradiation apparatus comprising:

a casing, a support member for carrying at least one irradiation bag containing a biological fluid, a light source comprising two banks of light disposed above and below the support member, and an agitation system for moving the support member, wherein the light source generates UVC light to inactivate pathogens and/or leukocytes and the agitation system moves the support member in an orbital path with predetermined amplitude suitable to expose the whole biological fluid to UVC placing at least an irradiation bag containing a biological fluid in an uncompressed state and lying flat and horizontally on the support member, irradiating the irradiation bag with UVC under orbital agitation and wherein irradiation bag on the support member is moved at a rotational frequency of about 108 rpm and above.

26. The process of claim 25, wherein the irradiation bag is filled with at most 30% of the volume capacity of the bag.

27. The process of claim 25, wherein the irradiation bag does not contain any photoinactivating substance.

28. The process of claim 25, wherein the light source emits light in the wavelength of from 200 to 350 nm.

29. The process of claim 25, wherein the light source provides a total energy of from 0.01 to 2 J/cm$^2$.

30. The process of claim 25, wherein the biological fluid is a platelet suspension.

31. The process of claim 30, wherein the platelet suspension comprises plasma.

32. The process of claim 30, wherein at least 25% of the plasma is substituted with a platelet storage solution.

33. The process of claim 30, wherein the biological fluid is plasma.

34. The process of claim 25, wherein the irradiation bag is filled with at most 10% of the volume capacity of the bag.

35. The process of claim 25, wherein the light source emits light in the wavelength of from 200 to 270 nm.

36. The process of claim 25, wherein the light source emits light in the wavelength of about 254 nm.

37. A process for inactivating pathogens and/or leukocytes in a biological fluid, comprising: providing an irradiation apparatus comprising:

a casing, a support member for carrying at least an one irradiation bag containing a biological fluid, a light source comprising two banks of light disposed above and below the support member, and an agitation system for moving the support member, wherein the light source generates UVC light to inactivate pathogens and/or leukocytes and the agitation system moves the support member in an orbital path with predetermined amplitude and a rotational frequency of 70 rpm and above suitable to expose the whole biological fluid to UVC placing at least an irradiation bag containing a biological fluid in an uncompressed state and lying flat and horizontally on the support member, irradiating the irradiation bag with UVC under orbital agitation, wherein the width and length of the orbital path are comprised between 0.2 and 8 cm.

38. The process of claim 37, wherein the path is circular and has a diameter of from 2 to 5 cm.

* * * * *